United States Patent
Schweigert et al.

(10) Patent No.: US 11,235,260 B2
(45) Date of Patent: Feb. 1, 2022

(54) METHOD FOR CONTROLLING A RECTIFICATION COLUMN

(71) Applicant: COVESTRO DEUTSCHLAND AG, Leverkusen (DE)

(72) Inventors: Mathias Schweigert, Cologne (DE); Achim Küpper, Leverkusen (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 496 days.

(21) Appl. No.: 16/322,990

(22) PCT Filed: Aug. 1, 2017

(86) PCT No.: PCT/EP2017/069397
§ 371 (c)(1),
(2) Date: Feb. 4, 2019

(87) PCT Pub. No.: WO2018/024711
PCT Pub. Date: Feb. 8, 2018

(65) Prior Publication Data
US 2019/0184304 A1    Jun. 20, 2019

(30) Foreign Application Priority Data
Aug. 4, 2016   (EP) .................................. 16182881

(51) Int. Cl.
*B01D 3/42* (2006.01)
*G05B 11/14* (2006.01)
(Continued)

(52) U.S. Cl.
CPC ............ *B01D 3/425* (2013.01); *B01D 3/4211* (2013.01); *C07C 17/383* (2013.01); *C07C 25/08* (2013.01);
(Continued)

(58) Field of Classification Search
CPC .... B01D 3/4211; B01D 3/425; B01D 3/4294; C07C 17/383; G05B 11/14; B05D 21/00
See application file for complete search history.

(56) References Cited

U.S. PATENT DOCUMENTS 3,464,895 A * 9/1969 Boyd .................. B01D 3/4255
                                                   203/2
3,830,698 A * 8/1974 Kleiss ................. B01D 3/4238
                                                   203/2
(Continued)

FOREIGN PATENT DOCUMENTS

DE           3906002 A1     8/1990

OTHER PUBLICATIONS

Zhou, Yuhong et al.; Optimizing Distillation Operation To Reduce Ethanol Content In Refined Methanol; Medium Nitrogen Fertilizer, Edition 2; Date Of Publication: Mar. 2012.

(Continued)

*Primary Examiner* — Jonathan Miller
(74) *Attorney, Agent, or Firm* — Donald R. Palladino

(57) ABSTRACT

The present invention relates to a method of controlling a concentration of a first component of a rectification column for separating a binary mixture of the first component with a second component on the basis of temperature measurements, wherein a control path defined by temperature sensors (T3, T2, T6) arranged in the longitudinal direction of the column is linearized with the aid of an estimated temperature profile, wherein a real temperature profile T*(h), determined by means of the temperature sensors, is approximated by a function T(h) in dependence on a column height h, wherein the column id divided into two sections along the column height h and the function T(h) is defined section by section on the basis, in each case, of a logistical function.

16 Claims, 2 Drawing Sheets

(51) Int. Cl.
  *C07C 17/383* (2006.01)
  *C07C 25/08* (2006.01)
  *G05D 21/00* (2006.01)
(52) U.S. Cl.
  CPC ............ *G05B 11/14* (2013.01); *G05D 21/00* (2013.01); *B01D 3/4294* (2013.01)

(56) References Cited

U.S. PATENT DOCUMENTS

| | | | | |
|---|---|---|---|---|
| 3,912,600 | A * | 10/1975 | Hatfield, Jr. | C08G 18/7664 203/73 |
| 4,024,027 | A * | 5/1977 | Boyd | B01D 3/4238 203/2 |
| 4,371,426 | A * | 2/1983 | DiBiano | B01D 3/4227 202/160 |
| 4,473,443 | A * | 9/1984 | Hobbs | B01D 3/425 202/160 |
| 4,526,657 | A * | 7/1985 | Hobbs | B01D 3/425 196/132 |
| 4,544,452 | A * | 10/1985 | Halliday | B01D 3/425 202/160 |
| 5,244,544 | A * | 9/1993 | Lang | B01D 3/4238 202/160 |
| 5,260,865 | A * | 11/1993 | Beauford | B01D 3/425 203/1 |
| 5,368,699 | A * | 11/1994 | Rhiel | B01D 3/4283 202/160 |
| 6,088,630 | A * | 7/2000 | Cawlfield | B01D 3/4255 202/160 |
| 6,413,378 | B1 * | 7/2002 | Kanauchi | B01D 3/40 196/100 |
| 6,605,190 | B1 * | 8/2003 | Salamon | B01D 1/2856 202/160 |
| 7,267,746 | B1 * | 9/2007 | Harris | B01D 3/141 196/111 |
| 7,292,899 | B2 * | 11/2007 | Dadebo | B01D 3/4211 62/643 |
| 8,078,323 | B2 * | 12/2011 | Meeuwssen | G05B 17/02 700/270 |
| 2004/0249512 | A1 * | 12/2004 | Meeuwssen | G05B 17/02 700/270 |
| 2007/0038333 | A1 * | 2/2007 | Dadebo | F25J 3/0295 700/270 |
| 2016/0202223 | A1 | 7/2016 | Ammouri et al. | |
| 2018/0164701 | A1 * | 6/2018 | De Best | G03F 7/70725 |

OTHER PUBLICATIONS

Achim Kienle: "Low-order dynamic models for ideal multicomponent distillation processes using nonlinear wave propagation theory", Chemical Engineering Science, vol. 55, No. 10, May 1, 2000 (May 1, 2000), pp. 1817-1828.

Paul S. Fruehauf, Donald P. Mahoney: Distillation Column Control Design Using Steady State Models: Usefulness and Limitations, ISA Transactions, vol. 32, 1993, p. 157-175.

W. L. Luyben, "Profile Position Control of Distillation Columns with Sharp Temperature Profiles" AIChE Journal, vol. 18, No. 1, 1972, pp. 238-240.

"Jörg Raisch: Mehrgrößenregelung im Frequenzbereich [Multiparameter Control in the Frequency Range], Oldenbourg Wissenschaftsverlag, Bedin, 1994.", chapter 9.1.8.

Zoller M. et al., "Zur Mehrgrossen-Temperaturregelung Von Destillationskolonnen", Automatisierungstechnische Praxis—ATP, Oldenbourg Industrieverlag, Munchen, DE, vol. 34, No. 3, Mar. 1, 1992, pp. 136-145.

Wolfgang, Marquardt et al., "Development of a linear distillation model from design data for process control", Computers & Chemical Engineering, vol. 18, Jan. 1, 1994, pp. S349-S353.

Brian Roffel et al., "A comparison of the performance of profile position and composition estimators for quality control in binary distillation", Computers & Chemical Engineering, vol. 27, No. 2, Feb. 1, 2003, pp. 199-210.

* cited by examiner

METHOD FOR CONTROLLING A RECTIFICATION COLUMN

CROSS REFERENCE TO RELATED APPLICATION

This application is a national stage application under 35 U.S.C. § 371 of PCT/EP2017/069397, filed Aug. 1, 2017, which claims the benefit of European Application No. 16182881.9, filed on Aug. 4, 2016, each of which is incorporated by reference herein.

FIELD

The present invention relates to a method of controlling a concentration of at least one first component in a rectification column for separation of a binary mixture of the first component and a second component based on temperature measurements.

BACKGROUND

Rectification columns are one of the most important production units in the chemical industry and are used for separation of mixtures of matter. The separation is energy-intensive. Both for economic and environmental reasons, energy consumption should be minimized. At the same time, it is necessary to comply with a specification which may include different aspects of the column. Typical examples are:
   product purity of the top product
   product purity of the bottom product
   withdrawal rate of the top product
   withdrawal rate of the bottom product
   feed rate of the feed stream.

The specification can arise either from demands imposed by a customer or from environmental regulations or result from later production steps.

Rectification, like distillation, is a thermal separation process. In the simplest case, a binary mixture is separated into its pure components. Separation can be implemented only up to a certain degree. In the case of rectification, the substance having lower vapor pressure is called high boiler, and that having higher vapor pressure low boiler. Rectification exploits the physical principle that the concentration of the low boiler in the vapor phase is higher than in the liquid phase. By contrast with distillation, this process is repeated several times, meaning that only a portion of a condensate formed at the top of the column is drawn off and collected, while a remaining portion of the tops condensate is fed back into the top of the column as what is called reflux. This can achieve a higher purity of the components of the mixture, i.e. the products of rectification. The concept of rectification can be explained by the ideal separation stage. At each separation stage, as in the case of distillation, a respective phase equilibrium is established.

The aim of rectification columns is the separating of the mixture of matter into pure substances or pure components. However, a small portion of the components in the mixture of matter is always present. The specification stipulates how high the concentration of secondary components may be in each case. A lower concentration of the secondary components is always associated with elevated energy expenditure. Therefore, maintaining a desired concentration of at least one of the pure substances or one of the components is the main aim of the control method. Also controlled are a level in a lower region of the column, called the bottom, in which the high boiler collects, a level in the upper region of the column, called the top, namely in a condensate vessel intended for the low boiler, and the pressure. The levels are controlled in order to prevent the column from flooding or running dry, and to maintain the material balance. The following manipulated variables are possible for the controlled variables of concentration, pressure and level:
   feed valve
   steam valve
   coolant valve
   distillate valve
   bottom product valve
   reflux valve.

Assignment of manipulated variables to controlled variables is made under physical/chemical considerations.

DE 39 06 002 A1 describes a model-assisted analysis and control unit for rectification columns, wherein a number of input parameters are predefined, namely temperature in the region where there is a relatively significant change in mass transfer, pressures in the column, feed rate per unit time, concentration of the feed, temperature of the feed, pressure of the feed, fill level of the distillate receiver, fill level in the bottom, and a combination of two parameters from the following four flow rates: reflux rate, distillate rate, heating steam rate and bottom product rate, in order to reduce any time delay between a moment of sampling and a display of the result, wherein the input parameters are processed in a model and with the aid of predefined equations, wherein the resulting output parameters, such as product composition and product rates, are in turn utilized directly for actuation of control elements.

The article "Low-order dynamic models for ideal multicomponent distillation processes using nonlinear wave propagation theory" by Achim Kienle discloses a simplified model for a rectification column, wherein the simplified model is based on a rigorous model from which a reduced "wave model" is derived, but this requires extensive information about substances used and apparatus properties, for example assumption of ideal separation stage at every tray, packing properties etc.

For the measurement of the concentration, it is possible to use a mass spectrometer, for example. However, corresponding instruments are very costly, and so temperature measurements are usually employed for control of concentration. A respective temperature sensor for control of concentration is (usually) not mounted at the top or bottom of the column since sensitivity in these regions is too low. Instead, it is possible to ascertain, using a steady-state model, the point at which sensitivity is at its greatest in relation to the concentration, as described, for example, in Paul S. Fruehauf, PE, Donald P. Mahoney: DISTILLATION COLUMN CONTROL DESIGN USING STEADY STATE MODELS: USEFULNESS AND LIMITATIONS, 1993. The point chosen is that at which the temperature deviation is about the same in both directions and sensitivity is sufficient.

Control of concentration via control of temperature by means of steam (feed in the bottom) and cooling liquid (feed at the top) is often unsatisfactory. Many columns have temperature profiles with a high temperature gradient at the respective mass transfer zones.

W. L. Luyben, in his article "Profile Position Control of Distillation Columns with Sharp Temperature Profiles", describes how the temperature profile is localized with the aid of a multitude of temperature sensors and the position of the temperature profile is used as process variable.

SUMMARY

It is now an object of the present invention to provide a further-improved means of controlling a concentration of a component of a binary mixture in a rectification column with a sharp temperature profile.

To achieve this object, the present invention provides a method and a system having the features of the respective independent claims. Configurations of the invention are apparent from the corresponding dependent claims and the description.

DETAILED DESCRIPTION

Figure 1:
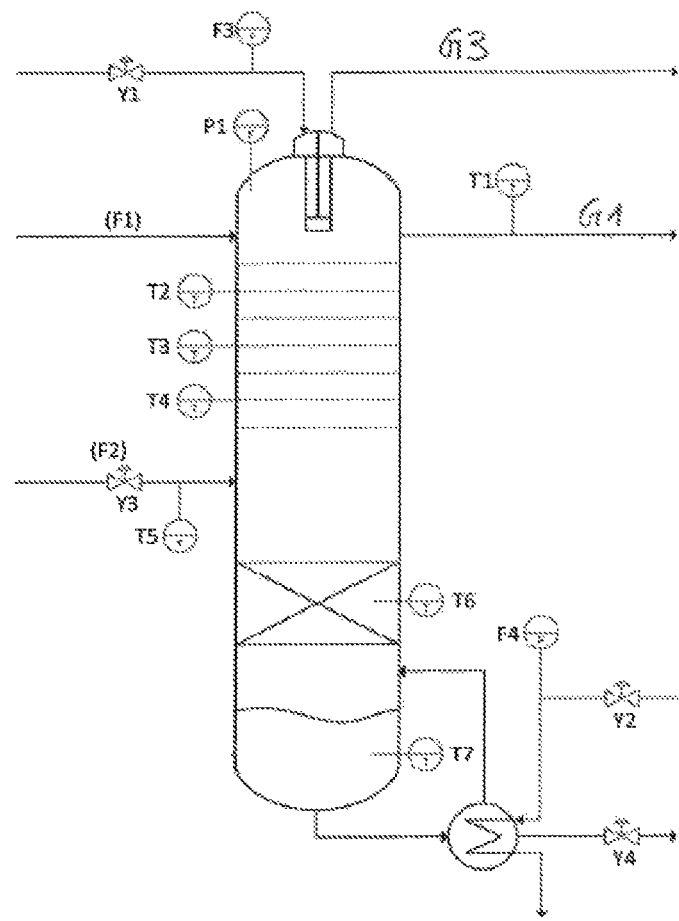
FIG. 1 is a schematic diagram of a rectification column that can be controlled in one embodiment of the method of the invention.

The present invention relates to a method of controlling a concentration of at least one first component in a rectification column for separation of a binary mixture of the first component and a second component based on temperature measurements. In this method, a control zone defined by temperature sensors arranged in longitudinal direction of the column is linearized with the aid of an estimate of a temperature profile, wherein a real temperature progression $T^*(h)$ determined by means of the temperature sensors is approximated by a function $T(h)$ as a function of a column height h, wherein the column is divided into two sections over the column height h and the function $T(h)$ is defined in sections on the basis of one logistic function in each section.

In the approximation of the temperature progression, it is also possible to determine or estimate a position of a mass transfer zone. The position of a mass transfer zone in turn serves as controlled variable in order to establish a desired position of the mass transfer zone connected to a desired product concentration. There is a defined relationship between product concentration and mass transfer zone, which has to be determined separately taking account of the substances used as components of the binary mixture. Product concentration may be understood to mean the concentration of the first component (for example top product), the concentration of the second components (for example bottom product) or both components. By means of the estimated temperature progression, it is possible, for example, to estimate the temperature at the top and use this as a basis to ascertain the concentration of the low boiler or the top product. The inventive use of logistic functions in the respective sections results in a linear relationship between each section of a mass transfer zone and a manipulated variable. The binary mixture results in two mass transfer zones, namely a first in the lower region of the column, i.e. below a feed or in the stripping section, and a second in the upper region of the column, i.e. above the feed or in the rectifying section. The manipulated variable for the rectifying section is a coolant rate; the manipulated variable for the stripping section is a steam rate. Controllers used may be standard PI/PID controllers.

In a possible configuration, the method of the invention is employed in a rectification column for separation of 1,2-dichlorobenzene (ODB) and $COCl_2$ (phosgene).

The advantage of the invention is firstly the distinctly lesser modeling complexity compared to modeling approaches known from the prior art, since only relatively few physical data (boiling temperatures) and column data (packing type etc.) are required, and secondly the lesser computing power required as a result. A rigorous process model as known from the prior art can easily contain several hundred differential equations, whereas the simplified process model presented here, depending on the number of measurement points or temperature sensors installed, is one to two orders of magnitude below that. This enables use in a productive system without using dedicated hardware. Rigorous models represent a technical mechanism with exact scientific methodology. They are created on the basis of physical, chemical or chemical engineering relationships. For example, a rigorous model recreates and simulates the rectification column or the process that proceeds therein, in that all known processes and reactions in the plant or in the column are simulated bit by bit physically and kinetically by characteristic lines, differential equations and balance equations. However, rigorous models are very costly to implement—too costly for most operations.

This aspect can have a major influence on the decision for or against such a productive system, since looking after an additional system in a plant which is operated for 50 years generates additional labor (operating system migration, maintenance, updates, lack of compatibility with new operating system) that can lead to shutdown of the system.

Under particular conditions, the estimated temperature at the top or bottom of the column can be used to calculate the concentration. It is a prerequisite that the concentration of secondary components is "small". But the concentration to be determined can have a lower concentration than that of the secondary components. In a configuration, the temperature profile can be visualized in a control panel assigned to the plant or to the column, such that, for example, effects on the top temperature by perturbations of any increases in temperature in the middle of the column can be better estimated.

There follows a description of the method of the invention using the example of a rectification column for separation of a mixture of phosgene and ODB, wherein phosgene is the first component and the low boiler in the mixture and ODB is the second component and the high boiler in the mixture. In the case of performance of rectification, phosgene accordingly collects preferentially in the upper region of the column, i.e. in the top of the column, and is accordingly the top product. By contrast, ODB as high boiler is enriched in the bottom of the column and is accordingly the bottom product. The estimate of the temperature profile, using the example of the rectification column for separation of phosgene and ODB, originates from observations during disturbance tests in a simulated system. A disturbance test is understood to mean an abrupt change in a manipulated variable, for example coolant rate at the top or steam rate at the bottom. In a temperature profile along the column which is obtained therefrom, for example along the column height, in particular, characteristic zones (or fronts, i.e. points with a high temperature gradient—cf. "Jörg Raisch: Mehrgrößenregelung im Frequenzbereich [Multiparameter Control in the Frequency Range], Oldenbourg Wissenschaftsverlag, Berlin, 1994.", chapter 9.18) with a high temperature gradient (based on height) are observed. At these points, there is significant mass transfer, and therefore these points are also referred to as mass transfer zones. If what is called a Wiener model, i.e. a linear system in which static nonlinearity occurs at the output, is assumed, the temperature characteristic can be represented in the form of static non-linearity. A characteristic feature of the progression is two S-shaped temperature progressions. The first covers the rectifying section between the top of the column (100% of the column height) and feed (about 24% of the column height), and the other the stripping section between the feed and bottom of the column (0%). The characteristic S shapes are maintained during the disturbance tests and have merely been moved along the column height. The result of this is the approach of approximating the behavior of the column during the disturbance tests, i.e. more particularly the temperature characteristics along the column height, by a shift in a static characteristic. Observations of the disturbance tests mentioned show the following: the breadth of variation of the steady-state gain in temperature, i.e. the breadth of variation of the temperature at a particular column height, is greater than the breadth of variation in the shift in the characteristic along the column height. For example, there is a significant change (i.e. by about 20%) at a temperature measurement point at about 40% of the column height only in the last disturbance. If, by contrast, in the disturbance tests, a particular temperature is monitored as a function of column height, an approximately linear progression is apparent. What is first being sought is the height (level) at which a particular temperature occurs. In a formal sense, the temperature for which the height is to be monitored must be between the boiling points of the first and second components, i.e. between the boiling points of the pure substances. One possible temperature is that which describes the position of the fronts. The real temperature progression $T^*(h)$ is known from a static simulation. This progression is now approximated in accordance with the invention by a function $T(h)$.

In a configuration of the invention, a transition of logistic functions is determined by a temperature at a feed to the column.

In one embodiment of the method of the invention, the respective logistic function chosen is a logistic function of the following form:

$$f(x) = \frac{e^x}{1+e^x} \quad (1)$$

The logistic function from equation (1) has an inflection point at $x=0$ and a range of values of $[0,1]$. In order to fit the logistic function to the temperature profile, the logistic function has to be shrunk and shifted. This gives rise to the following function with the given parameters:

$$T(h) = T_0 + v \frac{e^{(h-h_0)k}}{1+e^{(h-h_0)k}} \quad (2)$$

$h_0$ is a support vector that shifts the inflection point of the logistic function from 0 to the point $h_0$. The parameter $h_0$ ascertained online can be used to control the column since it shows a lesser degree of nonlinear behavior. k describes a shrinkage in the direction of the height of the column, $T_0$ describes a support vector of the temperature ($T_{min}$) and v a range of the temperature ($T_{max}-T_{min}$).

In a further embodiment of the method of the invention, the function $T(h)$ is defined as follows:

$$T(h) = \begin{cases} T_{ab}(h), & h < h_{feed} \\ T_v(h), & h \geq h_{feed} \end{cases} \quad (3)$$

where $T_{ab}(h)$ and $T_v(h)$ are each defined on the basis of a logistic function and $h_{feed}$ defines the column height at which the binary mixture, especially a solution consisting of equal parts of the first and second components, is fed to the column.

In a further configuration of the method of the invention:

$$T_v(h) = T_{0,v} + v_v \cdot \frac{e^{(h-h_{0,v})k_v}}{1+e^{(h-h_{0,v})k_v}} \quad (4)$$

$$T_{ab}(h) = T_{0,ab} + v_{ab} \cdot \frac{e^{(h-h_{0,ab})k_{ab}}}{1+e^{(h-h_{0,ab})k_{ab}}} \quad (5)$$

where the temperature has been normalized to the respective boiling temperatures $T\_1$ and $T\_2$ of the corresponding first and second components, with $0\%=T\_1$ and $100\%=T\_2$ and h normalized to an absolute column height H, where $T(h)=T_v(h)$ for $h \in [x\%, 100\%]$ in a rectifying section v, $T(h)=T_{ab}(h)$ for $h \in [0\%, x\%]$ in a stripping section ab of the column with $0<x<100$, and where $T_{0,v}$ and $T_{0,ab}$ are respective support vectors for the temperature, $v_v$ and $v_{ab}$ are a respective range for the temperature, $k_v$ and $k_{ab}$ are a respective shrinkage in the direction of the column height h, and $h_{0,v}$ and $h_{0,ab}$ are a respective support vector of the height h. $h_{0,v}$ and $h_{0,ab}$ correspond to the respective mass transfer zones in the rectifying section and in the stripping section of the column.

In one configuration of the method of the invention, x is chosen as 24. This corresponds to the relative height at which the feed valve is disposed. The specific feed height depends on a design of a respective column and can be calculated accurately with knowledge of the column design. The feed height defines the transition of the "part-functions" $T_{ab}(h)$ and $T_v(h)$.

The feed temperature determines the transition between the logistic functions.

In a further configuration, it is assumed that a range of values of $T_v(h)$ is between the boiling point of the first component and the feed temperature and hence $T_{0,v}(h)=0$ and $v_v=T_{feed}$.

The range of values of $T_v(h)$ is therefore to include only function values between the boiling point of the first component, i.e. the low boiler, and the feed temperature, i.e. the temperature at the feed. These give rise to the support vector and the range:

$$T_{0,v}=0 \quad (6)$$

$$v_v=T_{feed} \quad (7)$$

where $T_{feed}$ is normalized to the boiling temperature of the second component and the boiling temperature of the first component is set to "0".

In addition, in a further configuration, it is assumed that a range of values for $T_{ab}(h)$ is between the feed temperature $T_{feed}$ and the boiling point of the second component. The logistic function in the stripping section $T_{ab}(h)$ is to have a range of values between $T_{feed}$ and the boiling point of the second component, i.e. the high boiler. This gives:

$$T_{0,ab}=T_{feed} \quad (8)$$

$$v_{ab}=1-T_{feed} \quad (9)$$

where 1 corresponds to the boiling point normalized to the real boiling temperature of the second component or to the normalized boiling temperature of the second component, and $T_{feed}$ has been normalized to the boiling temperature of the second component.

In a further embodiment of the method of the invention, a respective shrinkage $k_v$ or $k_{ab}$ in the direction of the respective height is ascertained from a comparison of a slope of the logistic function f(x) at its inflection point and the measured temperature progression T*(h) at its inflection point, wherein the inflection point of T*(h) is calculated from an average of respective slopes at a respective inflection point of temperature progressions ascertained from disturbance tests. The shrinkage in the direction of the height $k_v$ or $k_{ab}$ is thus found from a comparison of the slope of the logistic function and the real temperature profile at the inflection point.

Thus, all parameters except $h_{0,v}$ and $h_{0,ab}$ have been determined. $h_{0,v}$ and $h_{0,ab}$ can be calculated via any temperature point T at a point h in the respective region or section of the column, i.e. in the rectifying section or in the stripping section, by solving a respectively corresponding equation of those above. Since, however, there are multiple temperature measurement points available, this is an over-represented equation system. A disadvantage of the method mentioned is that measurement inaccuracies, such as measurement noise and drift, are amplified when the temperature sensor is far removed from $h_{0,v}$ or $h_{0,ab}$. Rather than using just one equation for solution, the present invention proposes, in a further configuration, supplementing the above-described method with a parameter estimate in order to compensate for the disadvantages mentioned, where $h_{0,v}$ and $h_{0,ab}$ are each determined by a parameter estimate.

There follows an elucidation of the parameter estimate envisaged in accordance with the invention in general terms based on equation (2). Application is identical for the determination of $h_{0,v}$ and $h_{0,ab}$.

This involves first minimizing the least mean squares of the temperatures in relation to the parameter $h_0$:

$$\min_{h_0} = \|\vec{f} - \vec{T}\|_2^2 \text{ with}$$
$$\vec{T} = [T_1 ... T_i] \text{ with } i = 1, ... , n$$

$$\vec{f} = \begin{pmatrix} f_1(h_1, h_0) \\ \vdots \\ f_i(h_i, h_0) \end{pmatrix} = \begin{pmatrix} T_o + v \cdot \frac{e^{(h_1 h_0)k}}{1 + e^{(h_1 - h_0)k}} \\ \vdots \\ T_o + v \cdot \frac{e^{(h_1 - h_0)k}}{1 + e^{(h_i h_0)k}} \end{pmatrix} \tag{10}$$

$$\vec{h} = \begin{pmatrix} h(T_1) \\ \vdots \\ h(T_i) \end{pmatrix}$$

$$\vec{f}' = \frac{\partial \vec{f}}{\partial h_0} = \begin{pmatrix} -v \cdot \frac{ke^{(h_o+h_1)k}}{(e^{h_1 k} + e^{h_0 k})^2} \\ \vdots \\ -v \cdot \frac{ke^{(h_o+h_i)k}}{(e^{h_i k} + e^{h_0 k})^2} \end{pmatrix} \tag{11}$$

The function f(h) corresponds to equation (2), i.e. f(h)=T (h). The serial parameter i indicates the temperature measurement points present in each case in the rectifying region or section or in the stripping region or section. The parameter $h_0$, i.e. $h_{0,v}$ for the rectifying section and $h_{0,ab}$ for the stripping section is to be estimated. This is a nonlinear minimization problem since the parameter is in the exponent.

In one possible configuration of the method of the invention, the Gauss-Newton method is employed for estimation.

A residual vector $\vec{r}$ describes the current deviation of estimated from measured temperature and is formed as follows:

$$\vec{r} = \vec{f}(\vec{h}) - \vec{T} \tag{12}$$

The Gauss-Newton method also requires the partial derivative of $\vec{r}$ in $h_0$ $$\frac{\partial \vec{r}}{\partial h_0} = \frac{\partial \vec{f}}{\partial h_0} = \vec{f}' \tag{13}$$

This gives the Jacobi matrix $$D = \begin{pmatrix} \frac{\partial r_1}{\partial h_0} \\ \vdots \\ \frac{\partial r_n}{\partial h_0} \end{pmatrix} \tag{14}$$

The step width s is then calculated as follows:

$$s = (D^T D)^{-1} D^T \vec{r} \tag{15}$$

In the case of a parameter to be determined, D is a vector. Therefore, inter alia, the inversion from equation (15) with (13) is simplified to give:

$$(D^T D)^{-1} = \frac{1}{\|\vec{f}'\|_2^2} \tag{16}$$

$$s = \sum_{i=1}^{n} \frac{f_i' f_i}{\|\vec{f}'\|_2^2} \tag{17}$$

The next iteration value is $$h_0(t) = h_0(t-1) - s \tag{18}$$

The estimate of $h_0$ is used as controlled variable both for the rectifying section $h_{0,v}$=H1=$y_1$ as mass transfer zone and for the stripping section $h_{0,ab}$=H2=$y_2$ as mass transfer zone. Manipulated variables used are the coolant rate and the steam rate.

Further advantages and configurations of the invention are apparent from the description and the appended drawings.

It will be apparent that the features mentioned above and yet to be elucidated hereinafter are usable not just in the combination specified in the respective case but also in other combinations or on their own without leaving the scope of the present invention.

The invention is shown in schematic form in the drawings by means of a working example, and is described schematically and in detail hereinafter with reference to the drawings.

FIG. 1 shows a schematic diagram of a rectification column that can be controlled in one embodiment of the method of the invention.

Figure 2:
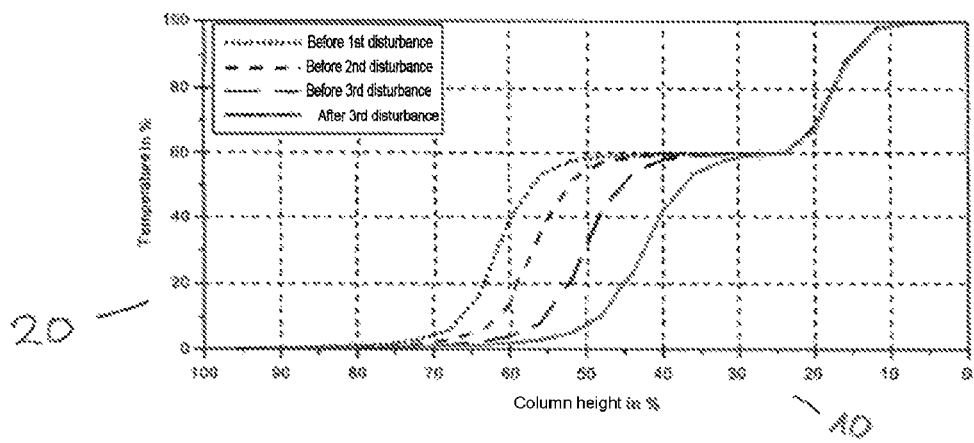
FIG. 2 shows illustrative temperature profiles of a rectification column after performance of disturbance tests, in each case by alteration of a coolant rate in each case as abruptly altered manipulated variable.

FIG. 2 shows illustrative temperature profiles of a rectification column after performance of disturbance tests, in each case by alteration of a coolant rate in each case as abruptly altered manipulated variable.

The rectification column shown in FIG. 1 is incorporated, for example, into a plant for preparation of toluene diisocyanate (TDI). The column shown has the task of supplying TDI reaction lines with vaporous phosgene. The column has an upper region, i.e. a top region or top, and a lower region, i.e. a bottom region or bottom. On performance of the rectification, phosgene as top product is enriched in the top, and ODB as bottom product accumulates in the bottom. Unlike in a standard column, the top product formed is not totally condensed, but drawn off in vaporous form. Therefore, the column shown in FIG. 1 does not have a condensate vessel. Instead, an inserted condenser is used. As a result, a reflux rate and a reflux ratio can be controlled only indirectly via a coolant rate. The phosgene is introduced firstly in the form of phosgene solution via a feed F2 having a feed valve Y3. Secondly, it is applied in pure form as liquid phosgene at the top F1 of the column. The phosgene solution consists in roughly equal parts of phosgene and the ODB solvent. Via a valve Y1 at the top, cooling liquid or coolant is fed in via a coolant feed F3. The cooling liquid can be removed again from the column via an outlet G3. A manometer P1 measures the pressure, which should be kept essentially constant. There are also multiple points or stages in the column, at each of which there are disposed temperature sensors T1 to T7. Via a valve Y2 and a feed F4, a heating medium or steam is supplied in the bottom of the column. A corresponding bottom product formed in the separation in the column is removed via a valve Y4. The feed F2 divides the column into two sections, namely an upper rectifying section between feed F2 and the top of the column, in the range from 24% to 100% of the column height in the case shown here, and a lower stripping section between feed F2 at the bottom of the column, i.e. between 0% and 24% in the case shown here. In the rectifying section, phosgene is enriched as low boiler. In the stripping section, the phosgene is parted from the ODB solvent. For control of concentration, the position of the temperature sensors in particular is important. The standard method is generally that neither the top temperature nor the bottom temperature is used directly for control, but rather temperatures between feed F2 and the respective product outlet. Useful temperatures in the rectifying section are the temperatures from temperature sensors T2 to T4 for the control of the top product concentration, and in the stripping section the temperature from temperature sensor T6 for the control of the bottom product concentration.

FIG. 2 shows a temperature profile T*(h) of the rectification column from FIG. 1 before and after performing disturbance tests, in each case by abruptly altering the coolant rate as manipulated variable.

On an abscissa 10 is a column height h in %, i.e. normalized to an absolute column height H. 100% corresponds here to a top of the column; 0% corresponds to a bottom of the column. On an ordinate 20 is plotted a temperature in %, where the temperature is standardized the respective boiling temperatures of phosgene and ODB. 0% corresponds here to the boiling temperature of phosgene and 100% corresponds to the boiling temperature of ODB.

A characteristic feature of the respective progressions shown is two S-shaped temperature progressions for each disturbance test per temperature profile. The first covers the rectifying section between the top of the column (100%) and feed F2 (24%), the other the stripping section between feed F2 and bottom of the column (0%). The characteristic S shapes are maintained during the disturbance tests and have merely been shifted along the column height, i.e. along the abscissa. This gives rise to the approach of approximating the behavior of the column in the disturbance tests by a shift in a static characteristic. The following becomes apparent from the observations of the disturbance tests: the range of variation of the steady-state gain in temperature (along the ordinate 20) is greater than the range of variation of the shift in the characteristic (along the abscissa 10). A temperature measurement point at 40% of the column height changes significantly by about 20% only in the last disturbance. If, by contrast, a temperature is monitored (for example 40% on the abscissa 10), an approximately linear progression is apparent. What is being sought is firstly the height (step) at which a particular temperature occurs. In a formal sense, the temperature for which the height is to be monitored must be between the boiling points of the pure materials, i.e. of phosgene and ODB. One option is the temperature which describes the position of the fronts in FIG. 2.

The invention claimed is:

1. A method of controlling a concentration of at least one first component in a rectification column for separation of a binary mixture of the first component with a second component based on temperature measurements, the method comprising:
 (a) linearizing a control zone defined by temperature sensors arranged in the longitudinal direction of the rectification column with the aid of an estimate of a temperature profile, and
 (b) approximating a real temperature progression T*(h) determined by means of the temperature sensors by a function T(h) as a function of a column height h, wherein:
  (i) the column is divided into two sections over the column height h, and
  (ii) the function T(h) is defined in sections on the basis of one logistic function in each section.

2. The method of claim 1, in which the logistic functions are formed on the basis of a logistic function of the following form:

$$f(x) = \frac{e^x}{1+e^x}.$$

3. The method of claim 1, wherein:

$$T(h) = \begin{cases} T_{ab}(h), & h < h_{feed} \\ T_v(h), & h \geq h_{feed} \end{cases}$$

where $T_{ab}(h)$ and $T_v(h)$ are defined on the basis of one logistic function each and $h_{feed}$ defines the column height at which a solution consisting of 40% by volume to 60% by volume of the first component and 40% by volume to 60% by volume of the second component is fed to the column.

4. The method of claim 3, in which:

$$T_v(h) = T_{0,v} + v_v \cdot \frac{e^{(h-h_{0,v})k_v}}{1+e^{(h-h_{0,v})k_v}}$$

$$T_{ab}(h) = T_{0,ab} + v_{ab} \cdot \frac{e^{(h-h_{0,ab})k_{ab}}}{1+e^{(h-h_{0,ab})k_{ab}}}$$

where T is normalized to boiling temperatures T_1 and T_2 of the corresponding first and second components, with 0%=T_1 and 100%=T_2 and h is normalized to an absolute column height H and T(h)=$T_v$(h) for h ∈ [x %, 100%] in a rectifying section v, $T(h)=T_{ab}(h)$ for $h \in [0\%, x \%]$ in a stripping section ab of the column height h with 0<x<100, and where $T_{0,v}$ and $T_{0,ab}$ are respective support vectors for the temperature, $v_v$ and $v_{ab}$ are a respective range for the temperature, $k_v$ and $k_{ab}$ are a respective shrinkage in the direction of the column height h, and $h_{0,v}$ and $h_{0,ab}$ are a respective support vector of the height h.

5. The method of claim 4, wherein x is 24.

6. The method of claim 4, in which the respective shrinkage $k_v$ or $k_{ab}$ in the direction of the respective height is ascertained from a comparison of a slope of the logistic function f(x) at its inflection point and the measured temperature progression T*(h) at its inflection point, wherein the inflection point of T*(h) is calculated from an average of respective slopes at a respective inflection point of temperature progressions ascertained from disturbance tests.

7. The method of claim 6, in which $h_{0,v}$ and $h_{0,ab}$ are each determined by a parameter estimate.

8. The method of claim 7, in which the Gauss-Newton method is employed for estimation.

9. The method of claim 4, in which a value range of $T_v(h)$ is between the boiling point of the first component and the feed temperature (T5) and hence $T_{0,v}(h)=0$ and $v_v=T_{feed}$ and a value range of $T_{ab}(h)$ is between the feed temperature (T5) and the boiling point of the second component and hence $T_{0,ab}(h)=T_{feed}$ and $v_{ab}=1-T_{feed}$, where 1 corresponds to the boiling point of the second component.

10. The method of claim 4, in which a value range of $T_v(h)$ is between the boiling point of the first component and the feed temperature (T5) and hence $T_{0,v}(h)=0$ and $v_v=T_{feed}$.

11. The method of claim 3, in which:

$$T_v(h) = T_{0,v} + v_v \cdot \frac{e^{(h-h_{0,v})k_v}}{1 + e^{(h-h_{0,v})k_v}}$$

$$T_{ab}(h) = T_{0,ab} + v_{ab} \cdot \frac{e^{(h-h_{0,ab})k_{ab}}}{1 + e^{(h-h_{0,ab})k_{ab}}}$$

where T is normalized to boiling temperatures T_1 and T_2 of the corresponding first and second components, with 0%=T_1 and 100%=T_2 and h is normalized to an absolute column height H and $T(h)=T_v(h)$ for $h \in [x \%, 100\%]$ in a rectifying section v, $T(h)=T_{ab}(h)$ for $h \in [0\%, x \%]$ in a stripping section ab of the column height h with 0<x<100, and where $T_{0,v}$ and $T_{0,ab}$ are respective support vectors for the temperature, $v_v$ and $v_{ab}$ are a respective range for the temperature, $k_v$ and $k_{ab}$ are a respective shrinkage in the direction of the column height h, and $h_{0,v}$ and $h_{0,ab}$ are a respective support vector of the height h, and in which a transition of the logistic functions is determined by a temperature (T5) at a feed to the column.

12. The method of claim 11, in which a value range of $T_v(h)$ is between the boiling point of the first component and the feed temperature (T5) and hence $T_{0,v}(h)=0$ and $v_v=T_{feed}$.

13. The method of claim 11, in which a value range of $T_{ab}(h)$ is between the feed temperature (T5) and the boiling point of the second component and hence $T_{0,ab}(h)=T_{feed}$ and $v_{ab}=1-T_{feed}$, where 1 corresponds to the boiling point of the second component.

14. The method of claim 1, in which a transition of the logistic functions is determined by a temperature (T5) at a feed to the column.

15. The method as claimed of claim 1, in which the first component comprises 1,2-dichlorobenzene (ODB) and the second component comprises $COCl_2$ (phosgene).

16. A system comprising a rectification column that executes the method of claim 1.

* * * * *